US006637587B2

(12) United States Patent
Britton

(10) Patent No.: US 6,637,587 B2
(45) Date of Patent: *Oct. 28, 2003

(54) DISPOSAL UNIT FOR MEDICAL SHARPS

(75) Inventor: Richard Berkeley Britton, Charlottesville, VA (US)

(73) Assignee: Hetex Holdings, LLC, Charlottesville, VA (US)

( * ) Notice: Subject to any disclaimer, the term of this patent is extended or adjusted under 35 U.S.C. 154(b) by 232 days.

This patent is subject to a terminal disclaimer.

(21) Appl. No.: 09/791,804

(22) Filed: Feb. 26, 2001

(65) Prior Publication Data

US 2001/0019023 A1 Sep. 6, 2001

Related U.S. Application Data

(63) Continuation-in-part of application No. 09/106,455, filed on Jun. 30, 1998, now Pat. No. 6,315,113.

(51) Int. Cl.[7] ............................................. B65D 81/24
(52) U.S. Cl. ..................... 206/210; 206/365; 206/366; 206/370; 604/110
(58) Field of Search ................... 206/210, 366, 206/365, 370; 604/110; 204/275

(56) References Cited

U.S. PATENT DOCUMENTS

| 4,328,632 | A | * | 5/1982 | Beers ............................ 42/95 |
| 5,038,929 | A | * | 8/1991 | Kubofcik ..................... 206/210 |
| 5,047,224 | A | * | 9/1991 | Dhooge ..................... 423/437.1 |
| 5,372,252 | A | * | 12/1994 | Alexander ................... 206/210 |
| 5,441,622 | A | * | 8/1995 | Langford ..................... 204/273 |
| 5,887,807 | A | * | 3/1999 | Beinecke ....................... 241/36 |
| 6,142,303 | A | * | 11/2000 | Dendy et al. ............... 206/568 |
| 6,315,113 | B1 | * | 11/2001 | Britton et al. .............. 206/210 |
| 6,332,534 | B1 | * | 12/2001 | Hammett ..................... 206/366 |

* cited by examiner

*Primary Examiner*—Weilun Lo
*Assistant Examiner*—Michael G Mendoza

(57) ABSTRACT

This disposal unit comprises a means for applying a dissolvent to medical sharps, thereby converting the hazardous and possibly contaminated sharps into metallic ions existing in solution within the dissolvent. The dissolvent is absorbed in a perforatable pad and the sharp is plunged into the pad whereby the sharp makes contact with the dissolvent which effects its disposal. After the sharp has been dissolved, the syringe or handle for the sharp falls into an antiseptic solution and is disinfected. After disinfection, a net facilitates removal of the residual plastic parts for recycling.

9 Claims, 2 Drawing Sheets

DISPOSAL UNIT FOR MEDICAL SHARPS

This is a Continuation-In-Part of patent application Ser. No. 09/106,455 filed Jun. 30, 1998 and issued as U.S. Pat. No. 6,315,113.

FIELD OF THE INVENTION

This invention pertains to means and methods for the disposal of medical sharps such as syringe needles, scalpels, lancets, and the like.

BACKGROUND OF THE INVENTION

With the advent of many types of medical implements designed for disposal after a single use such as syringes, lancets, scalpels et cetera, there has arisen a hazard of disease spread, and particularly diseases that have no cure and are ultimately fatal. Such diseases are now being spread from accidental wounds occuring during disposal of contaminated medical sharps. By far the bulk of such disposables are syringes.

A common size of disposable medical syringe for insulin use has an injectable volume of 3/10 cc and is fitted with a 29 gauge (0.013" diameter) stainless steel needle 0.5 inches long. Another common size is a 1.0 cc syringe. Such syringes retail for about 16 cents each in a quantity of 100. It is believed that hospitals pay about 6 cents each to purchase these sizes in bulk. For this reason, it was decided from the onset that a practical, marketable disposal means for medical sharps must cost considerably less per unit than the preceding figures.

SUMMARY OF THE INVENTION

This invention addresses safer means for the disposal of syringe needles, in particular, and additionally, for the disposal of lancets and scalpels. The major application for the disposal unit described herein is expected to be medical and dental clinics, emergency vehicles, private homes, and field hospitals. As described in the parent patent application, the gist of this invention is the chemical dissolution of a medical sharp with a specially formulated solution which is referred to herein as a dissolvent. The dissolvent is typically composed of an acid such as hydrochloric, a salt such as ferric chloride, and water. The strength of these components is adjusted for the speed of dissolution desired in tradeoff with the safety desired for potential human contact with the dissolvent. In prototypes of the invention, syringe needles have been completely dissolved and left not a trace in substantially less than five minutes.

It must be emphasized that human contact with the dissolvent is not life threatening. The most that such contact may cause is a minor chemical burn. There is a far greater risk when a person receives an accidental scratch from a syringe needle, scalpel, or lancet which may be contaminated with the fatal AIDS virus.

The invention herein comprises a method of applying a dissolvent to medical sharps. The means of dissolvent application is typically a disposing block made of a soft, absorbant material similar to a common household cellulosic sponge. The block is saturated with a dissolvent capable of chemically dissolving metallic medical sharps, and typically within a few minutes depending upon the strength of the dissolvent used. Disposal of a sharp is accomplished by thrusting the sharp into the block where it remains until it is totally dissolved and no longer hazardous. The handle or body of the sharp then drops into a disinfecting solution from which is can later be removed for safe disposal and possible recycling along with ordinary plastics.

BRIEF DESCRIPTION OF THE DRAWING FIGURES

DETAILED DESCRIPTION OF THE PREFERRED EMBODIMENTS

In this invention, a chemical dissolving agent for metallic medical sharps is contained in reticular passages of a perforable disposal block or pad composed of a material such as plastic that is not attacked by said agent, the medical sharps being disposed of by insertion into the block whereby the sharp becomes exposed to the chemical dissolving agent. The chemical dissolving agent within the block is capable of dissolving a typical syringe needle within a few minutes, and of dissolving a scalpel blade in about an hour.

The block may be immersed in a disinfectant so that a syringe body or scalpel handle will fall by gravity into said solution, thereby becoming soaked and disinfected, after the related metallic sharp has been dissolved away.

Singlehanded use by, for example a nurse that wishes to quickly dispose of a used syringe, is facilitated by an automatic cover that opens a container containing the disposal block when a person moves their hand near the disposal unit to insert a sharp.

A typical disposal unit will comprise a disposal block in combination with a container and cover. The disposal block is expected to cost one to two cents for each syringe or scalpel treated. At facilities where labor is cheap, the container can be designed for reuse while the block and associated chemicals can be designed for replacement when they have become depleted.

Figure 1:
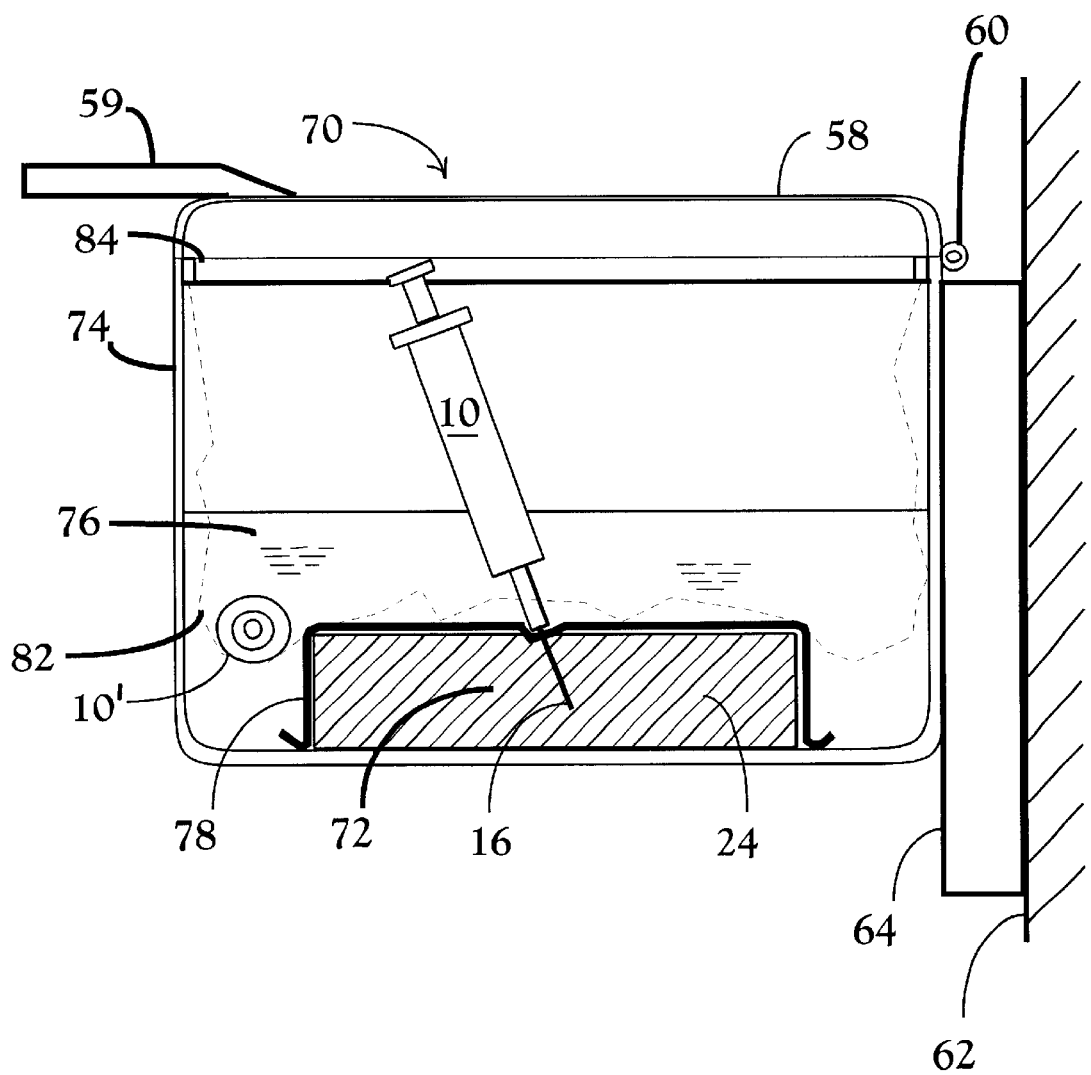
FIG. 1 is a sectional view of a disposal unit designed for wall mounting and in which a syringe has been inserted for disposal.

FIG. 1 illustrates a wall mounted disposal unit 70 for disposing of syringe needles, scalpel blades and the like, generally referred to as medical sharps. The disposal unit comprises a means for dissolving sharps by an improved means of contacting a sharp with disinfectants and with chemical dissolving agents referred to herein as dissolvents. In this device, dissolvent 24 is contained within the reticular passages of a block 72 of a plastic material that is not attacked by dissolvent. One such material is cellulose as is used for common kitchen sponges. The block is retained in a container 74 of sufficient depth to contain a quantity of chemical disinfectant 76. One effective disinfectant is chlorine bleach, and another is a Lysol® solution. The disinfectant 76 should cover the surface of the block, whereby the disinfectant can contact and disinfect the surfaces of items such as a syringe 10 and needle 16, which has been forcibly thrust into block 72 for disposal. After needle 16 dissolves, syringe 10 will fall and submerge in the chemical disinfectant 76.

A film 78 of a plastic material not attacked by either dissolvent 24 or disinfectant 76 is placed over the block to minimize mixing of disinfectant with dissolvent. The container has a cover 58 attached to it, the attachment typically being by means of a hinge 60. The disposal unit can be fitted with a mechanism to automatically raise cover 58 at the approach of a person's hand.

Cover can be also be fitted with a lift tab 59 operable by the back of one's hand or by an elbow whereby cover 58 is operated singlehandedly as is often needed in a medical facility. A third way to lift cover 58 singlehandedly is by the use of a foot treadle, not shown but well known for foot operation to raise the lid of a trash can.

Figure 2:
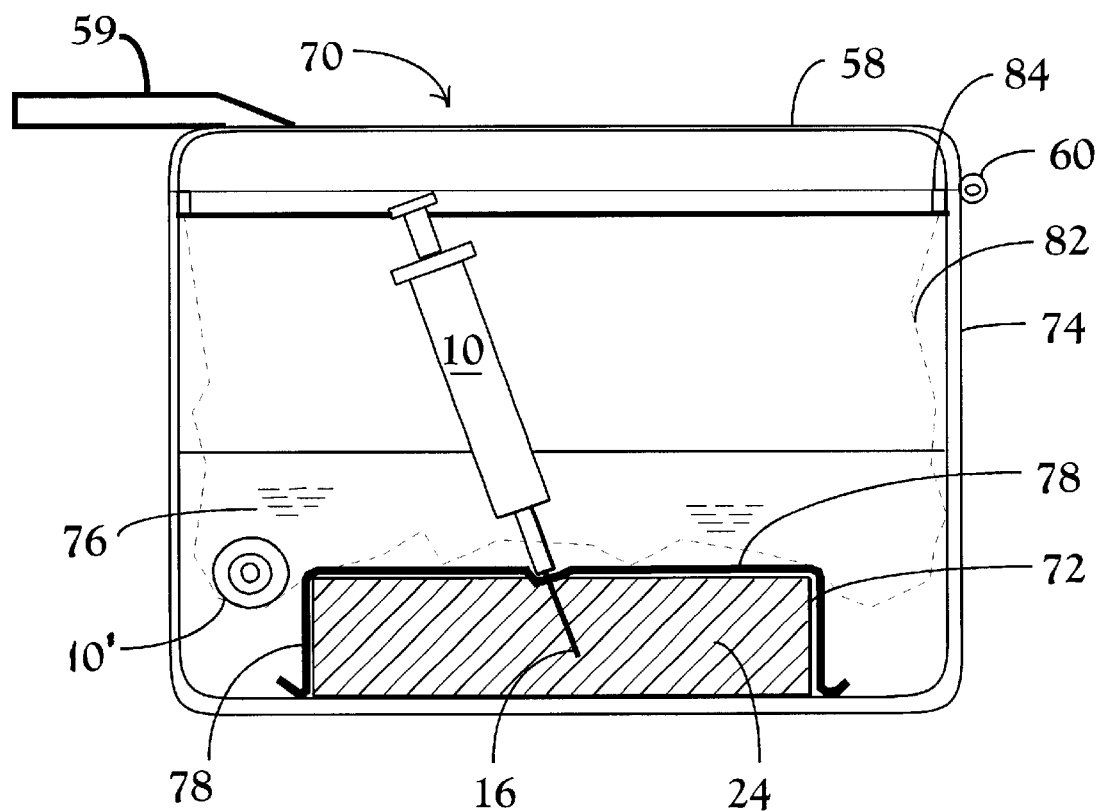
FIG. 2 is a sectional view of a disposal unit fitted into a container designed for use on a horizontal surface such as a table top.

Also illustrated in FIGS. 1 and 2 a netting 82 is retained by a loose internal ring 84. As container 74 fills with syringe bodies 10' with their needles 16 dissolved away, netting 82 may be lifted out of the container with the aid of ring 84 to remove the syringe bodies for conventional disposal.

FIG. 2 illustrates a disposal unit for use on a table top or other horizontal surface where such use is permitted by local regulations. Other aspects of the unit in FIG. 2 are similar to those of FIG. 1.

I claim:

1. A disposal medical sharps disposal unit comprising:

a liquid solution absorbed in reticular passages of a three dimensional, perforatable block or pad inert to said solution, said liquid solution being a chemical dissolvent capable of dissolving metallic medical sharps, the block or pad being used for the insertion and disposal of medical sharps.

2. A disposal unit as in claim 1 further comprising a container in which said block or pad is placed, a disinfectant liquid in said container at a level sufficient to cover said block or pad, and a film of plastic separating said disinfectant from said block or pad to prevent mixing of said disinfectant with said dissolvant, said plastic being unreactive to said dissolvant and unreactive to said disinfectant.

3. A disposal unit as in claim 2 further comprising a cover fitted to said container by a hinge, said cover being capable of being lifted by an extremity while said extremity is holding a medical sharp.

4. A disposal unit as in claim 2 further comprising a cover fitted to said container, said cover being openable by a proximity sensor which detects the approach of a person's hand.

5. A disposal unit as in claim 1 wherein said block is covered by a film of plastic inert to said dissolvent and said block is designed for attachment to a vertical wall.

6. A disposal unit as in claim 5 wherein said film of plastic is self sealing and holes resulting from insertion of medical sharps self seal after said sharp is dissolved.

7. A disposal unit as in claim 5 wherein said dissolvent dries upon contact with air and self seals any holes in said film of plastic which result from being pierced by sharps.

8. A disposal unit as in claim 2 further comprising a cover fitted to said container by a hinge, said cover being operable by an attached foot treadle.

9. A disposal unit as in claim 2, further comprising a plastic net draped over said block and means for lifting said net out of said container for the purpose of removing disposed or spent syringe bodies and scalpel handles from said disinfectant solution, said net being inert to said disinfectant solution.

* * * * *